United States Patent [19]
Joseph

[11] Patent Number: 6,048,881
[45] Date of Patent: Apr. 11, 2000

[54] METHOD OF TREATING CHRONIC PAIN ASSOCIATED WITH MUSCLE SPASMS, TENDONITIS AND SCIATICA

[76] Inventor: William K. Joseph, 241 Central Park West, #7C, New York, N.Y. 10024

[21] Appl. No.: 09/241,179

[22] Filed: Feb. 1, 1999

[51] Int. Cl.⁷ .................................................. A61K 31/44
[52] U.S. Cl. ............................................................ 514/356
[58] Field of Search ............................................. 514/356

[56] References Cited

U.S. PATENT DOCUMENTS

| | | | |
|---|---|---|---|
| 4,639,465 | 1/1987 | Pollack et al. | 514/419 |
| 5,053,396 | 10/1991 | Blass | 514/45 |

OTHER PUBLICATIONS

H. Winter Griffith, M.D., "Vitamins Herbs, Minerals & Supplements", *Fisher Books*, pp. 52–54, 1998.

Randall Swain and Barbara Kaplan, "Vitamins As Therapy In the 1990s", *JABFP*, vol. 8 No. 3 pp. 206–216, 1995.

Glenn S. Rothfeld, M.D. and Suzanne LeVert, "Natural Medicine for Back Pain", *Rodale Press, Inc.*, pp. 98–99, 1996.

Lama Nazer and Carlos C. da Camara, "Nocturnal Leg Cramps: A Management Review", *Pharmacy Times*, pp. 75–80, 1998.

*Primary Examiner*—William R. A. Jarvis
*Attorney, Agent, or Firm*—Hoffman & Baron, LLP; Irving N. Feit

[57] ABSTRACT

The invention is a method of treating chronic pain associated with muscle spasms, tendonitis and sciatica comprising administering to a human patient an effective amount of niacin.

4 Claims, No Drawings

METHOD OF TREATING CHRONIC PAIN ASSOCIATED WITH MUSCLE SPASMS, TENDONITIS AND SCIATICA

FIELD OF INVENTION

The present invention relates to a method for treating chronic pain associated with muscle spasms, tendonitis and sciatica by administering to a human patient an effective amount of niacin.

BACKGROUND OF THE INVENTION

Chronic pain associated with conditions such as muscle spasms, tendonitis and sciatica is not only very painful to the individual, but is usually very difficult to treat. Inadequate treatment of chronic pain can be debilitating to humans.

Muscle spasms are violent, involuntary contractions of a muscle or a group of muscles. They affect a large segment of the population and are often very painful. The pain resulting from muscle spasms often is chronic, i.e. lasts for one day or even longer. By contrast, the pain associated with leg cramps, which usually radiates from the calf, and can last from a few seconds up to ten minutes. See for example, Weiner et al., *JAMA* 244:2332–2333 (1980).

Conditions involving muscle spasms may result from injury or trauma to the affected muscle or nerve that innervates that muscle. Some conditions involving muscle spasms include lower back and cervical spine syndromes and whiplash injuries.

Other painful conditions include sciatica and tendonitis. Sciatica is a condition characterized by pain radiating from the muscles in the back into the buttocks. Sciatica may result from trauma to the spinal cord or to the sciatic nerve. Another condition characterized by chronic pain is tendonitis, which is an inflammation of tendons and of tendon-muscle attachments.

The debilitating effects of chronic pain are not only a source of anxiety and distress for the individual, but represent a tremendous cost to society. For example, workers suffering from chronic pain are frequently absent from work for weeks or even longer. This poses a great expense to the employer in sick-time coverage, disability pay and to society in lost productivity.

At present, a variety of medicinals are used in an attempt to relieve or correct these conditions associated with chronic pain. These medicinals include muscle relaxants such as methocarbamol, carisoprodol and mephenesin. Nonsteroidal anti-inflammatory agents such as ibuprofen, aspirin, and indomethacin are also used in conjunction with muscle relaxants for treating muscle spasms, tendonitis and sciatica. However, these medicinals provide, at most, partial relief and do not provide relief considered adequate by most people.

Niacin, which is also known as Vitamin $B_3$, is an important biochemical component that acts as a catalyst for cellular reactions and synthesis of important coenzymes such as nicotine adenosine dinucleotide and nicotine adenosine dinucleotide phosphate. These coenzymes play a key role in glycolysis, fatty acid synthesis and in deamination of amino acids.

Niacin is one of the oldest pharmacologic agents used in the treatment of hyperlipidemia. At doses of 3–6 g/day, it is highly effective in reducing elevated levels of plasma cholesterol and triglycerides. Niacin is known to inhibit adipose tissue lipolysis, reduce plasma free fatty acid levels and decreases very low density lipoprotein. This has been shown to be a benefit in preventing nonfatal myocardial infarction due to arteriosclerotic heart disease.

Large doses of niacin (1–6 g/day) have also been used as adjunctive therapy for the treatment of conditions associated with deficient circulation. Some examples include peripheral vascular disease, vascular spasm, migraine headache, Mèniére's syndrome and vertigo.

Niacin has also been recommended for a variety of other conditions. Some examples include schizophrenia, chronic brain syndrome, acne, leg cramps and alcoholism.

The consumption of niacin is usually accompanied by facial and truncal flushing associated with warmth and tingling in these areas. These side effects usually occur in nearly all users shortly after ingestion of doses as small as 75 mg of niacin. Facial and truncal flushing are believed to be the result of peripheral vasodilation, predominantly of cutaneous vessels in the face, neck and chest. This niacin flush reaction is believed to be mediated by prostaglandins (e.g., prostacyclin), and is generally considered harmless.

Based on the foregoing, there is a need for a more effective treatment of chronic pain associated with muscle spasms, tendonitis and sciatica. Accordingly, it is one of the objects of the present invention to provide a superior treatment for chronic pain associated with muscle spasms, tendonitis and sciatica.

SUMMARY OF THE INVENTION

It has now been discovered that this and other objectives can be achieved by the present invention, which provides a method for treating a human suffering from chronic pain associated with muscle spasms, tendonitis and sciatica comprising administering to the human an effective amount of niacin.

DETAILED DESCRIPTION OF THE INVENTION

As used herein, a muscle spasm is a sudden, violent, involuntary contraction of a muscle or a group of muscles, attended by muscle hyperactivity and persistent or chronic pain of long duration. For example, the chronic pain can last at least one day, and often lasts at least one week or even longer. Such muscle spasms may interfere with function, producing involuntary movement and distortion. Chronic pain associated with muscle spasms generally occurs in the back, neck and shoulder.

The method of the present invention can also be used to treat tendonitis. As used herein tendonitis is defined as inflammation of tendons and of tendon-muscle attachments.

Tendonitis can occur anywhere in the body where tendons are located. It often occurs in joints of the shoulder, elbow, foot and knee. For example, tendonitis includes inflammation and calcification of the subacromial or subdeltoid bursa, which results in chronic pain, tenderness, and limitation of motion in the shoulder.

Tendonitis may be caused by trauma. For example, tendonitis ossificans traumatica is a condition where areas of ossification develop in tendons as a result of trauma.

The method of the present invention can also be used to treat sciatica. As used herein, sciatica refers to pain anywhere along the course of the sciatic nerve and is characterized by pain radiating from the back into the buttocks. Sciatica is most commonly caused by prolapse of the intervertebral disk.

For the purposes of the present invention, niacin includes both nicotinic acid (pyridine-3-carboxylic acid) and the amide form of nicotinic acid, niacinamide. Niacin is commercially available from health food stores and pharmacies, and is made by various manufactures. For example niacin is available as Niacor® from Upsher-Smith pharmaceuticals.

The present invention also includes pharmaceutically acceptable salts of niacin. Some examples of pharmaceutically acceptable salts include those salt-forming acids and bases which do not substantially increase the toxicity of the compound. Some examples of suitable salts include salts of alkali metals such as magnesium, potassium and ammonium. Salts of mineral acids include hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

An effective amount as used herein is that amount effective to achieve the relief or palliation of chronic pain associated with muscle spasms, tendonitis and sciatica. Preferably, niacin is administered in an amount that limits the most common side effects discussed above.

The minimal dosage of niacin for a human is the lowest dosage which achieves the desired result. For example, niacin is administered at a minimal dosage of at least about 50 mg, preferably at least about 100 mg, more preferably at least about 150 mg and most preferably at least about 200 mg.

Maximal dosage for a human is the highest dosage which does not cause undesirable or intolerable side effects. For example, niacin is administered at a maximal dosage of at least about 6 g/day, preferably at least about 4 g/day, more preferably at least about 2 g/day and most preferably at least about 1 g/day.

The daily dose of niacin can be divided into multiple daily doses, such as two to five divided daily doses, in order to minimize side effects. In any event, the practitioner is guided by skill and knowledge in the field, and the present invention includes without limitation dosages which are effective to achieve the described effect. Preferably niacin should be taken on an empty stomach.

Administering niacin can be accomplished in a variety of ways. In humans, niacin can be administered orally or enterally which is the preferred route of delivery. Formulations such as tablets, capsules, pills, troches, elixirs, suspensions, syrups, wafers, chewing gum and the like can be employed to provide niacin. Immediate release preparations of niacin are most preferred.

Niacin can also be administered by the parenteral route. For example, niacin can easily be administered intravenously (e.g., intravenous injection). Intravenous administration can be accomplished by mixing niacin in a suitable pharmaceutical carrier (vehicle) or excipient as understood by practitioners in the art.

The invention has been developed based on the Applicant's unexpected observation that niacin is useful in treating chronic pain associated with conditions such as muscle spasms, tendonitis and sciatica in humans. Applicant is also unaware of any treatment regimen which employs niacin for treating these conditions.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method of treating chronic pain associated with muscle spasms, tendonitis, or sciatica in a human suffering therefrom consisting essentially of orally administering to said human an effective amount of niacin.

2. The method in accordance with claim 1 wherein the niacin is administered orally.

3. The method in accordance with claim 2 wherein the niacin is administered in an amount from about 50 mg to about 6 gm/day.

4. The method in accordance with claim 3 wherein the niacin is administered in two to five daily doses.

* * * * *